United States Patent [19]
Kita et al.

[11] Patent Number: 6,013,826
[45] Date of Patent: Jan. 11, 2000

[54] METHOD FORMATION OF A CARBON-CARBON BOND

[75] Inventors: Yasuyuki Kita, Osaka; Atsunori Sano, Saitama; Takahiro Yamaguchi, Saitama; Masahisa Oka, Saitama; Masato Matsugi; Kentoku Gotanda, both of Osaka, all of Japan

[73] Assignee: Waco Pure Chemical Industries, Osaka, Japan

[21] Appl. No.: 09/063,825

[22] Filed: Apr. 22, 1998

[30] Foreign Application Priority Data

Apr. 24, 1997 [JP] Japan ................................ 9-121668

[51] Int. Cl.[7] ............................................. C07C 255/00
[52] U.S. Cl. ............................................. 558/358; 534/838
[58] Field of Search ............................... 534/838; 558/358

[56] References Cited

U.S. PATENT DOCUMENTS

| | | | |
|---|---|---|---|
| 2,586,995 | 2/1952 | Robertson et al. | 534/838 |
| 2,615,915 | 10/1952 | Ladd | 558/358 |

FOREIGN PATENT DOCUMENTS 57-45735   9/1982   Japan .

OTHER PUBLICATIONS

Kita et al., Tetrahedron Letters, 38(20), 3549–3552, May 19, 1997.

D.P. Curran, et al.; "Additions of Malononitrile Radicals to Alkenes: New Examples of 1,2–Asymmetric Induction in Iodine and Phenylselenium Transfer Reactions," *J. Am. Chem. Soc.*, 114, pp. 4436–4437, 1992.

D.P. Curran, et al.; "Atom Transfer Addition and Annulation Reactions of Propargyl Iodomalononitrile," *Tetrahedron*, vol. 48, No. 11, pp. 2157–2174, 1992.

"Zur Bilding Von Dicyancarben Aus Brommalonitril Und Triäthylamin" Tetrahedron Letters No. pp. 1415–1417, 1996. Pergamon Press Ltd. Printed in Great Britain.

Peter Boldt, et al.; "1.1–Dicyan–cyclopropane", *Chem. Ber.*, pp. 1281–1288, 1967.

Peter Boldt, et al.; "γ–Lactone aus Alkenen," *Chem.*, 102, pp. 4157–4163, 1969.

Peter Boldt, et al.; "The Stereochemistry of Free Radical Additions of Alkyl Halides to Alkenes—1, " *Tetrahedron*, vol. 26, pp. 3591–3615, 1970.

H.M. Bartels, et al.; "Einfache Synthese einiger Spiro[2.4]heptan–4,4,7,7–tetracarbonitrile," *Chem. Ber.*, 114, pp. 3997–4004, 1981.

H.M. Bartels, et al.; "Radikalische Addition von Brommalononitril an Allene," *Liebigs Ann. Chem.*, pp. 40–46, 1981.

K. Oshima, et al.; "New Method of Radical Formation.—Radical Reactions with $R_3SnH$–$Et_3B$ System—," Department of Industrial Chemistry, Faculty of Engineering, Kyoto University, pp. 40–51, 1989.

*Primary Examiner*—Fiona T. Powers
*Attorney, Agent, or Firm*—Armstrong, Westerman, Hattori, McLeland & Naughton

[57] ABSTRACT

A method for an addition reaction with the formation of an additional carbon—carbon bond comprising reacting an α-halogeno carboxylic acid derivative with an alkene in the presence of a catalyst shown by the general formula (1):

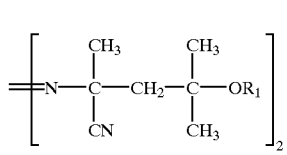

(1)

wherein $R_1$ is a lower alkyl group.

17 Claims, No Drawings

METHOD FORMATION OF A CARBON-CARBON BOND

BACKGROUND OF THE INVENTION

The present invention relates to a novel catalyst for the formation of a carbon—carbon bond and a method for the formation of a carbon—carbon bond using the said catalyst.

Formation of a carbon—carbon bond using radical reactions is one of the important tactics in organic synthesis. It has been considered that the reaction can desirably be conducted under mild conditions as far as possible in order to conduct clean reactions without causing side reactions. However, azobisisobutyronitrile (AIBN) which has been well known as an initiator for radical reactions has a possibility of causing side reactions because it requires heat for the generation of radicals. A radical addition reaction under photo-irradiation can be conducted even at room temperature or lower, but it is not suitable to a large scale synthesis. Recently, a reaction using a Lewis acid as a radical initiator at lower temperature has been developed, but this method cannot be applied to a substrate containing an acid sensitive functional group.

SUMMARY OF THE INVENTION

The present invention has been completed under the circumstances mentioned above, and the object of the invention is to provide a catalyst for the formation of a carbon—carbon bond, particularly for an addition reaction with the formation of an additional carbon—carbon bond, which can control side reactions under mild reaction conditions and also stereoregularity and further, to provide a method for the formation of a carbon—carbon bond, particularly a method for an addition reaction with the formation of an additional carbon—carbon bond using the said catalyst.

The present inventors have made extensive study for establishing a reaction which makes it possible to control side reactions and stereoregularity, particularly to control simply and completely stereoregularity, whereby attention has been paid to the fact that the azo compound shown by the general formula [1], which has been used in the synthesis of polymers, can generate effectively radicals at lower temperature, and the inventors have found that all of the problems mentioned above can be solved by using the compound as a catalyst for the formation of a carbon—carbon bond, particularly for an addition reaction with the formation of an additional carbon—carbon bond to reach finally the present invention.

The characteristics of the present invention are;

(1) A catalyst for the formation of a carbon—carbon bond comprising an azo compound shown by the general formula [1]

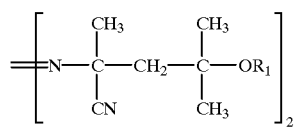

[1]

(wherein $R_1$ is a lower alkyl group).

(2) A catalyst for an addition reaction with the formation of an additional carbon—carbon bond comprising an azo compound shown by the general formula [1]

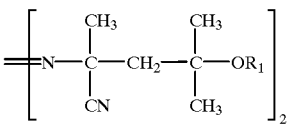

[1]

(wherein $R_1$ is a lower alkyl group).

(3) A method for the formation of a carbon—carbon bond comprising conducting a reaction in the presence of a catalyst mentioned in (1).

(4) A method for an addition reaction with the formation of an additional carbon—carbon bond comprising subjecting an α-halogeno carboxylic acid derivative and an alkene to a reaction in the presence of a catalyst mentioned in (1).

(5) A method for production of a compound shown by the general formula [4]

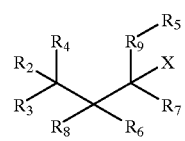

[4]

(wherein X is a halogen atom, at least one of $R_3$ and $R_4$ are an alkyloxycarbonyl group, an aralkyloxycarbonyl group, an aryloxycarbonyl group, an acyloxy group, an acyl group, a cyano group, a carbamoyl group or a carboxyl group, and the rest and $R_2$ are independently a hydrogen atom, an alkyl group, an aryl group which may have a substituent, an alkoxy group, an aralkyloxy group, an aryloxy group or a hydroxy group, $R_5$ is a hydrogen atom, an alkyl group, a haloalkyl group, an aryl group which may have a substituent, an aralkyl group which may have a substituent, an aliphatic heterocyclic group, an aromatic heterocyclic group, an alkyloxycarbonyl group, a hydroxyalkyloxycarbonyl group, an aralkyloxycarbonyl group, an aryloxycarbonyl group, an acyloxy group, an acyl group, an alkoxy group, an aralkyloxy group, an aryloxy group, group, a cyano group, an amino group, a carbamoyl group, a hydroxyl group, a sulfonic acid group, an aldehydo group or a carboxyl group, $R_6$ is a hydrogen atom, a halogen atom, an alkyl group, an aralkyl group which may have a substituent, an alkyloxycarbonyl group, a hydroxyalkyloxycarbonyl group, a hydroxyl group or a carboxyl group, $R_9$ is an alkylene group or a bond, $R_7$ is a hydrogen atom, an alkyl group, a carboxyl group, an alkyloxycarbonyl group, a hydroxyalkyloxycarbonyl group or a hydroxyl group and $R_8$ is a hydrogen atom, a halogen atom or an alkyl group, and $R_7$ and $R_8$ may form together an aliphatic ring) comprising reacting an α-halogeno carboxylic acid derivative shown by the general formula [2]

[2]

(wherein the symbols have the same meaning as above) with an alkene shown by the general formula [3]

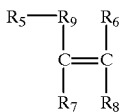

(wherein the symbols have the same meaning as above) in the presence of a catalyst shown by the general formula [1]

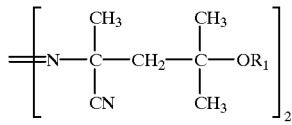

(wherein $R_1$ is a lower alkyl group).

DESCRIPTION OF THE PREFERRED EMBODIMENTS

The lower alkyl group shown by $R_1$ in the general formula [1] includes one having 1 to 4 carbon atoms such as a methyl group, an ethyl group, a propyl group and a butyl group, among which a methyl group is preferable.

The α-halogeno carboxylic acid derivative used in present invention includes one shown by the following general formula [2]

(wherein X is a halogen atom, at least one of $R_3$ and $R_4$ are an alkyloxycarbonyl group, an aralkyloxycarbonyl group, an aryloxycarbonyl group, an acyloxy group, an acyl group, a cyano group, a carbamoyl group or a carboxyl group, and the rest and $R_2$ are independently a hydrogen atom, an alkyl group, an aryl group which may have a substituent, an alkoxy group, an aralkyloxy group, an aryloxy group or a hydroxy group).

The halogen atom shown by X in the general formula [2] includes chlorine, bromine and iodine, among which bromine is preferable. The alkyloxycarbonyl group shown by $R_3$ and $R_4$ may be straight chain or branched chain and includes one having 2 to 19 carbon atoms such as a methyloxycarbonyl group, an ethyloxycarbonyl group, a propyloxycarbonyl group, a butyloxycarbonyl group, a pentyloxycarbonyl group, a hexyloxycarbonyl group, a heptyloxycarbonyl group, an octyloxycarbonyl group, a dodecyloxycarbonyl group, an octadecyloxycarbonyl group, a tert-butyloxycarbonyl group and a 2-ethylhexyloxycarbonyl group. The aralkyloxycarbonyl group includes one having 8 to 20 carbon atoms such as a benzyloxycarbonyl group and a phenethyloxycarbonyl group. The aryloxycarbonyl group includes one having 7 to 20 carbon atoms such as a phenyloxycarbonyl group and a naphthyloxycarbonyl group. The acyloxy group includes one having 2 to 18 carbon atoms, which is derived from carboxylic acids, such as an acetyloxy group, a propionyloxy group, a butyryloxy group, a pentanoyloxy group, a hexanoyloxy group, a heptanoyloxy group, an octanoyloxy group and a benzoyloxy group. The acyl group includes one having 1 to 18 carbon atoms, which is derived from carboxylic acids, such as a formyl group, an acetyl group, a propionyl group, a butyryl group, a pentanoyl group, a hexanoyl group, a heptanoyl group, an octanoyl group and a benzoyl group.

The alkyl group shown by $R_2$ to $R_4$ may be straight chain, branched chain or cyclic and includes one having 1 to 20 carbon atoms such as a methyl group, an ethyl group, an n-propyl group, an isopropyl group, an n-butyl group, an isobutyl group, a tert-butyl group, a sec-butyl group, a pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, a heptyl group, an octyl group, a nonyl group, a decyl group, an undecyl group, a dodecyl group, a hexadecyl group, an octadecyl group, a cyclopropyl group, a cyclopentyl group and a cyclohexyl group. The aryl group, which may have a substituent such as an alkoxy group, a vinyl group, a halogen atom, an amino group, a hydroxy group and a carboxyl group, includes a phenyl group, a tolyl group, a xylyl group, a naphthyl group, an anthryl group, a 4-ethylphenyl group, a 4-methoxyphenyl group, a 4-vinylphenyl group, a 4-chlorophenyl group, an aminophenyl group, a hydroxyphenyl group and a carboxylphenyl group. The alkoxy group may be straight chain or branched chain and includes one having 1 to 18 carbon atoms, preferably 1 to 8 carbon atoms, such as a methoxy group, an ethoxy group, a propoxy group, a butoxy group, a pentyloxy group, a hexyloxy group, a heptyloxy group, an octyloxy group, a 2-propoxy group, a tert-butoxy group and a 2-ethylhexyloxy group. The aralkyloxy group includes one having 7 to 20 carbon atoms such as benzyloxy group and a phenethyloxy group. The aryloxy group includes one having 6 to 20 carbon atoms such as a phenoxy group and a naphtyloxy group.

The alkene of the present invention, which is to be reacted with an α-halogeno carboxylic acid derivative includes one shown by the general formula [3]

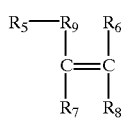

(wherein $R_5$ is a hydrogen atom, an alkyl group, a haloalkyl group, an aryl group which may have a substituent, an aralkyl group which may have a substituent, an aliphatic heterocyclic group, an aromatic heterocyclic group, an alkyloxycarbonyl group, a hydroxyalkyloxycarbonyl group, an aralkyloxycarbonyl group, an aryloxycarbonyl group, an acyloxy group, an acyl group, an alkoxy group, an aralkyloxy group, an aryloxy group, a cyano group, an amino group, a carbamoyl group, a hydroxyl group, a sulfonic acid group, an aldehydo group or a carboxyl group; $R_6$ is a hydrogen atom, a halogen atom an alkyl group, an aralkyl group which may have a substituent, an alkyloxycarbonyl group, a hydroxyalkyloxycarbonyl group, a hydroxyl group or a carboxyl group; $R_9$ is an alkylene group or a bond; $R_7$ is a hydrogen atom, an alkyl group, a carboxyl group, an alkyloxycarbonyl group, a hydroxyalkyloxycarbonyl group or a hydroxyl group and $R_8$ is a hydrogen atom, a halogen atom or an alkyl group, and $R_7$ and $R_8$ may form together an aliphatic ring).

The aralkyl group which may have a substituent such as an alkyloxycarbonyl group shown by $R_5$ and $R_6$ in the general formula [3] includes one having 7 to 20 carbon atoms its substituted one whose ring has a substituent such as a benzyl group, a phenethyl group, a 3-phenylpropyl group and a 3-(4-methyloxycarbonylphenyl)propyl group. The alkyloxycarbonyl group shown by $R_5$, $R_6$ and $R_7$ may be straight chain or branched chain and includes one having 2 to 19 carbon atoms such as a methyloxycarbonyl group, an ethyloxycarbonyl group, a propyloxycarbonyl group, butyloxycarbonyl group, a pentyloxycarbonyl group, a hexyloxycarbonyl group, a heptyloxycarbonyl group, an octyloxycarbonyl group, a dodecyloxycarbonyl group, an octadecyloxycarbonyl group, a tert-butyloxycarbonyl group and a 2-ethylhexyloxycarbonyl group. The hydroxyalkyloxycarbonyl group shown by $R_5$, $R_6$ and $R_7$ includes one having 2 to 19 carbon atoms in which the hydrogen atom of the alkyl group of the above-mentioned alkyloxycarbonyl group is substituted by a hydroxyl group, such as a hydroxymethyloxycarbonyl group, a hydroxyethyloxycarbonyl group, a hydroxypropyloxycarbonyl group, a hydroxybutyloxycarbonyl group, a hydroxypentyloxycarbonyl group, a hydroxyhexyloxycarbonyl group, a hydroxyheptyloxycarbonyl group, a hydroxyoctyloxycarbonyl group, a hydroxydodecyloxycarbonyl group and a hydroxyoctadecyloxycarbonyl group.

The alkyl group shown by $R_5$ may be straight chain, branched chain or cyclic and includes one having 1 to 20 carbon atoms such as a methyl group, an ethyl group, an n-propyl group, an isopropyl group, an n-butyl group, an isobutyl group, a tert-butyl group, a sec-butyl group, a pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, a heptyl group, an octyl group, a nonyl group, a decyl group, an undecyl group, a dodecyl group, a hexadecyl group, an octadecyl group, a cyclopropyl group, a cyclopentyl group and a cyclohexyl group. The haloalkyl group includes one having 1 to 20 carbon atoms in which the above-mentioned alkyl group is halogenated (e.g. fluorinated, chlorinated, brominated or iodinated), such as a chloromethyl group, a bromomethyl group, a trifluoromethyl group, a 2-chloroethyl group, a 3-chloropropyl group, a 3-bromopropyl group, a 3,3,3-trifluoropropyl group, a 2-perfluorooctylethyl group, a perfluorooctyl group, a 1-chlorodecyl group, a 1-chlorooctadecyl group and an 8-iodooctyl group. The aryl group, which may have a substituent such as an alkoxyl group, a halogen atom, an amino group, a hydroxyl group, a sulfo group and a carboxyl group, includes a phenyl group, a tolyl group, a xylyl group, a naphthyl group, an anthryl group, a 4-ethylphenyl group, a 4-methoxyphenyl group, a 4-vinylphenyl group, a 4-chlorophenyl group, an aminophenyl group, a hydroxyphenyl group, a sulfophenyl group and a carboxyphenyl group. The aliphatic heterocyclic group is preferably a 5- or 6-membered one and includes one containing 1 to 3 hetero atoms such as a nitrogen atom, an oxygen atom and a sulfur atom, such as a pyrrolidyl-2-on group, a piperidinyl group, a piperazinyl group and a morpholinyl group. The aromatic heterocyclic group is preferably a 5- or 6-membered one and includes one having 1 to 3 hetero atoms such as a nitrogen atom, an oxygen atom and a sulfur atom, such as a pyridyl group, an imidazolyl group, a thiazolyl group, a furanyl group and a piranyl group. The aralkyloxycarbonyl group includes one having 8 to 15 carbon atoms such as a benzyloxycarbonyl group and a phenethyloxycarbonyl group. The aryloxycarbonyl group includes one having 7 to 20 carbon atoms such as a phenyloxycarbonyl group and a naphthyloxycarbonyl group. The acyloxy group includes one having 2 to 18 carbon atoms, which is derived from carboxylic acids, such as an acetyloxy group, a propionyloxy group, a butyryloxy group, a pentanoyloxy group, a hexanoyloxy group, a heptanoyloxy group, an octanoyloxy group and a benzoyloxy group. The acyl group includes one having 1 to 18 carbon atoms, which is derived from carboxylic acids, such as a formyl group, an acetyl group, a propionyl group, a butyryl group, a pentanoyl group, a hexanoyl group, a heptanoyl group, an octanoyl group and a benzoyl group. The alkoxy group may be straight chain or branched chain and includes one having 1 to 18 carbon atoms, preferably 1 to 8 carbon atoms, such as a methoxy group, an ethoxy group, a propoxy group, a butoxy group, a pentyloxy group, a hexyloxy group, a heptyloxy group, an octyloxy group, a 2-propoxy group, a tert-butoxy group and a 2-ethylhexyloxy group. The aralkyloxy group includes one having 7 to 20 carbon atoms such as benzyloxy group and a phenethyloxy group. The aryloxy group includes one having 7 to 15 carbon atoms such as a phenoxy group and a naphtyloxy group.

The alkyl group shown by $R_6$, $R_7$ and $R_8$ may be straight chain or branched chain and it is preferably a lower alkyl group having 1 to 6 carbon atoms, such as a methyl group, an ethyl group, an n-propyl group, an isopropyl group, an n-butyl group, an isobutyl group, a tert-butyl group, a sec-butyl group, a pentyl group, an isopentyl group, a neopentyl group, a tert-pentyl group, a 3,3-dimethylbutyl group, a 1,1-dimethylbutyl group, a 1-methylpentyl group, an n-hexyl group and an isohexyl group.

The halogen atom shown by $R_6$ and $R_8$ includes chlorine, bromine, fluorine and iodine.

The aliphatic ring formed together by $R_7$ and $R_8$ includes a ring formed through an alkylene group having 3 to 10 carbon atoms and the ring may be monocyclic or polycyclic. The specific examples of the ring thereof are a norbornene ring, a cyclopentene ring, a cyclohexene ring, a cyclooctene ring and a cyclodecene ring. The alkylene shown by $R_9$ may be straight chain or branched chain and includes one having 1 to 10 carbon atoms such as a methylene group, an ethylene group, a propylene group, a butylene group, a 2-methylpropylene group, a pentylene group, a 2,2-dimethylpropylene group, a 2-ethylpropylene group, a hexylene group, a heptylene group, an octylene group, a 2-ethylhexylene group, a nonylene group and a decylene group.

The alkene of the above general formula [3] may be symmetric or asymmetric and includes ethylenically unsaturated aliphatic hydrocarbons having 2 to 20 carbon atoms such as ethylene, propylene, butylene and isobutylene; unsaturated alicyclic hydrocarbons having 3 to 20 carbon atoms such as norbornene, cyclopentene, cyclohexene, cyclooctene and cyclodecene; α-ethelenically unsaturated aromatic hydrocarbons having 8 to 20 carbon atoms such as styrene, 4-methyl styrene, 4-ethyl styrene and 4-methoxy styrene; alkenyl esters having 3 to 20 carbon atoms such as vinyl formate, vinyl acetate, vinyl propionate and isopropenyl acetate; halogeno-containing ethylenically unsaturated compounds having 2 to 20 carbon atoms such as vinyl chloride, vinylidene chloride, vinylidene fluoride; ethylenically unsaturated carboxylic acids having 3 to 20 carbon atoms such as acrylic acid, methacrylic acid, itaconic acid, maleic acid, fumaric acid, crotonic acid, citraconic acid, mesaconic acid, vinyl acetic acid, allyl acetic acid and vinyl benzoic acid (those acid may be in a form of an alkaline metal salt such as sodium salt and potassium salt or ammonium salt); ethylenically unsaturated carboxylic acid esters having 4 to 20 carbon atoms such as methyl methacrylate, ethyl methacrylate, propyl methacrylate, butyl methacrylate, 2-ethylhexyl methacrylate, lauryl methacrylate, stearyl methacrylate, vinyl methacrylate, aryl methacrylate, phenyl methacrylate, benzyl methacrylate, methyl acrylate, ethyl acrylate, butyl acrylate, 2-ethylhexyl acrylate, lauryl acrylate, stearyl acrylate, vinyl acrylate, dimethyl itaconate, diethyl itaconate, dimethyl maleate, diethyl maleate, dimethyl fumarate, diethyl fumarate, methyl crotonate, ethyl crotonate, vinyl crotonate, dimethyl citraconate, diethyl citraconate, dimethyl mesaconate, diethyl mesaconate, methyl 3-butenoate, 2-hydroxyethyl methacrylate, 3-hydroxypropyl methacrylate, 2-hydroxypropyl methacrylate, 2-hydroxyethyl acrylate, 3-hydroxypropyl acrylate and 2-hydroxypropyl acrylate; cyano-containing ethylenically unsaturated compounds having 3 to 20 carbon atoms such as acrylonitrile, methacrylonitrile and allyl cyanide; ethylenically unsaturated amide compounds having 3 to 20 carbon atoms such as acrylamide and methacrylamide; ethylenically unsaturated aldehydes having 3 to 20 carbon atoms such as acrolein and crotonaldehyde; ethylenically unsaturated sulfonic acids having 2 to 20 carbon atoms such as vinyl sulfonic acid and 4-vinylbenzene sulfonic acid (those acid may be in a form of an alkaline metal salt such as sodium salt and potassium salt); ethylenically unsaturated aliphatic amines having 2 to 20 carbon atoms such as vinylamine and allylamine; ethylenically unsaturated aromatic amines having 8 to 20 carbon atoms such as vinylaniline; ethylenically unsaturated aliphatic heterocyclic amines having 5 to 20 carbon atoms such as N-vinyl pyrrolidone and vinyl piperidine; ethylenically unsaturated aromatic heterocyclic amines having 5 to 20 carbon atoms such as vinyl pyridine and 1-vinyl imidazole; ethylenically unsaturated alcohols having 3 to 20 carbon atoms such as allyl alcohol and crotyl alcohol and ethylenically unsaturated phenols having 8 to 20 carbon atoms such as 4-vinyl phenol.

Among the alkene mentioned above, those shown by the general formula [3'] are preferable.

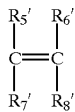

[3']

(wherein $R_5'$, $R_6'$, $R_7'$ and $R_8'$ are independently a hydrogen atom, a lower alkyl group, a carboxyl group, an aryl group which may have a substituent, a lower alkyloxycarbonyl group, a lower hydroxyalkyloxycarbonyl group or a lower acyloxy group and $R_7'$ and $R_8'$ may form together an aliphatic ring).

In the above general formula [3'], the lower alkyl group means an alkyl having 1 to 6 carbon atoms, a lower alkyloxycarbonyl group may be straight chain or branched chain and includes one having 2 to 7 carbon atoms, a lower hydroxyalkyloxycarbonyl group includes one having 2 to 7 carbon atoms, a lower acyloxy group means an acyloxy group having 2 to 7 carbon atoms, which is derived from the corresponding carboxylic acid, and other groups and the specific examples of the groups are the same as those mentioned concerning the alkene shown by the general formula [3].

With the use of the catalyst shown by the general formula [1], the above mentioned α-halogeno carboxylic acid derivative is reacted with, for instance, the alkene shown by the general formula [3] or [3'] in a suitable solvent, if necessary, under inert gas streams in a conventional manner, whereby an addition reaction with the formation of an additional carbon—carbon bond proceeds to give an adduct shown by the general formula [4] or [4']

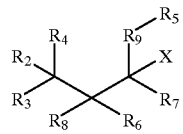

[4]

(wherein X, $R_2,R_3,R_4,R_5,R_6,R_7,R_8$ and $R_9$ have the same meaning as above),

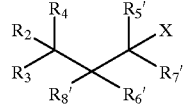

[4']

(wherein X, $R_2$, $R_3$, $R_4$, $R_5'$, $R_6'$, $R_7'$, and $R_8'$, have the same meaning as above).

A treatment after the reaction can be conducted in accordance to a conventional after-treatment procedure, and purification of the resulting compound may be conducted after a so-far known method such as various kinds of chromatography and recrystallization.

An amount of the α-halogeno carboxylic acid derivative and that of the alkene to be used in the present invention are not specifically limited, and preferably, the alkene is used in an equimolar amount or more relative to the α-halogeno carboxylic acid derivative.

An amount of the catalyst for the formation of a carbon—carbon bond to be used is not specifically limited and can be suitably selected according to the progress of a reaction and cost, and it is selected from a range generally of 0.01 equivalent or more, preferably 0.1 to 5 equivalent, relative to the α-halogeno carboxylic acid derivative.

A reaction solvent includes a hydrocarbon such as toluene, xylene, benzene, cyclohexane, n-hexane and n-octane, a halogenated hydrocarbon such as methylene chloride, dichloroethane and trichloroethane, an ester such as methyl acetate, ethyl acetate, n-butyl acetate and methyl propionate, a ketone such as acetone, methyl ethyl ketone, methyl isobutyl ketone, tert-butyl methyl ketone and cyclohexanone, and an ether such as dimethyl ether, diethyl ether, diisopropyl ether, dimethoxy ethane, tetrahydrofuran and dioxane, and those solvent may be used alone or in suitable combination of two or more thereof.

The inert gas, which may be used, if necessary, includes nitrogen gas and argon gas.

Though the reaction temperature is not specifically limited, when it is too low, reaction speed becomes slower because only a small amount of azo group is decomposed, and when it is too high, by-products are tend to be produced and the selective addition reaction does not proceed smoothly, and thus it is selected generally from a range of lower than 70° C., preferably −30 to 60° C., more preferably −10 to 30° C.

The reaction time depends upon reaction conditions such as reaction temperature, the kinds of α-halogeno carboxylic acid derivative, the alkene and the catalyst for the formation of a carbon—carbon bond and concentration of the catalyst, and it is determined by monitoring the progress of the reaction by thin-layer chromatography (TLC), high-performance liquid chromatography (HPLC), etc. and generally, it is suitably selected from a range of 10 minutes to 170 hours.

As for the α-halogeno carboxylic acid derivative and the alkene, use may be made of commercially available ones or one produced after a conventional manner.

As for the azo compound shown by the general formula [1], use may be made of commercially available ones or one produced by a method disclosed in U.S. Pat. No. 2,586,995 or JP-A 50-13328(Japanese Patent Publication—Kokai-).

In the above reaction, an additional carbon—carbon bond is formed by binding the carbon atom to which a halogen atom of the α-halogeno carboxylic acid derivative shown by the above general formula [2] is bound to the carbon atom to which $R_9$—$R_5$ of the alkene shown by the above general formula [3] is bound, whereby the compound (the adduct) shown by the above general formula [4] is produced.

The resulting product (the adduct) contains a halogen atom in its molecule, which is reactive, and thus by reacting the product with, for instance, a lower alcohol, the corresponding alkoxy derivative in which the halogen atom is replaced with the alkoxy group is obtained.

The characteristic feature of the present invention lies in using the azo compound shown by the above general formula [1], which has been used as a radical initiator, as a catalyst for the formation of a carbon—carbon bond, particularly for an addition reaction with the formation of an additional carbon—carbon bond. The said azo compound has such effect that it can generate radicals around room temperature and thus requires no heating for generation of radicals like azobisisobutyronitrile so far generally having been used as a radical initiator and therefore control of side reactions and stereo regulation become possible. Namely, use of the catalyst shown by the above general formula [1] of the present invention can afford such a remarkable effect thus making it possible to conduct, as the case may be, a position selective addition reaction of the α-halogeno carboxylic acid derivative including one shown by the above general formula [2] to the alkene including one shown by the above general formula [3] to give predominantly a specific stereo isomer (e.g. syn-isomer or anti-isomer) of the compound (adduct) shown by the above general formula [4] in high yield.

The present invention is further explained in the following referring to Examples and Reference Examples, but the present invention is not limited thereto by any means.

EXAMPLES

In the following Examples, Reference Examples and Tables, the abbreviations used have the meanings as indicated below. V-70: 2,2'-azobis(4-methoxy-2,4-dimethylvaleronitrile) (manufactured and sold by Wako Pure Chemical Industries, Ltd.; Trade Name)

AIBN: azobisisobutyronitrile
BPO: benzoyl peroxide
$Et_3B$: triethylboran
IPE: diisopropyl ether
TBME: tert-butylmethyl ether Example 1

Styrene in an amount of 10 mmol, bromomalononitrile in an amount of 10 mmol and methylene chloride in an amount of 10 ml were admixed with one another and V-70 in an amount of 5 mol % was added thereto, followed by conducting a reaction at room temperature (25° C.) for 12 hours with stirring.

After the reaction, the solvent was removed by distillation and 2-propanol in an amount of 10 ml was added to the residue to precipitate the object product. The product was recovered by filtration, washed and dried to give the object adduct (yield: 79%).

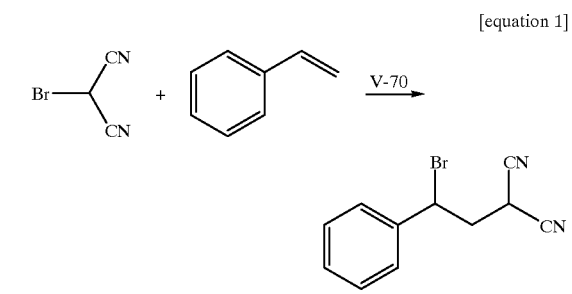

[equation 1]

Control Examples 1 to 3

A reaction was conducted in the same manner as in Example 1 except radical initiators and reaction times as shown in Table 1. The results together with that of Example 1 are shown in Table 1.

Control Example 4

A reaction was conducted in the same manner as in Control Example 1 except increasing the reaction temperature up to 40° C., whereby (1,2-dibromoethyl)benzene was obtained.

TABLE 1

| Example No. | Radical initiator | Reaction time (hr) | Yield (%) |
|---|---|---|---|
| Example I | V-70 | 12 | 79 |
| Control Example 1 | AIBN | 24 | not reacted |
| Control Example 2 | BPO | 24 | not reacted |
| Control Example 3 | $Et_3B$ | 18 | 44 |

As is clear from the above result, when a typical azo type radical initiator AIBN (Control Example 1) and a typical peroxide type radical initiator BPO (Control Example 2) were used, the reaction did not proceed at room temperature (25° C.) and, when $Et_3B$ (Control Example 3) was used, though the object adduct could be obtained, its yield was low because $Et_3B$ was considered to accelerate the decomposition of bromomalononitrile. On the contrary, when V-70 (Example 1) was used as a radical initiator, the object adduct could be obtained in a yield of 79% under the same reaction conditions.

Further, in Control Example 1, no AIBN radical was generated at room temperature and thus the same reaction was conducted under heating (40° C.) in order to generate the radicals (Control Example 4), whereupon no object adduct was obtained but only (1,2-dibromoethyl)benzene (dibromo type compound) shown in the following formula was predominantly obtained.

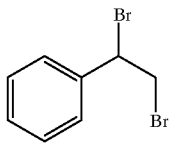

Also from the above result, it can be understood that the method of the present invention is clearly superior to the conventional method using AIBN.

Example 2 to 5

The same reaction as in Example I except the reaction temperature and the reaction time as shown in Table 2 was conducted to give the object adduct. The result together with that in Example 1 is shown in Table 2.

| Example No. | Reaction temperature (° C.) | Reaction time (hr) | Yield (%) |
| --- | --- | --- | --- |
| Example 1 | 25 | 12 | 79 |
| Example 2 | 10 | 24 | 71 |
| Example 3 | 10 | 36 | 80 |
| Example 4 | 0 | 24 | 56 |
| Example 5 | 0 | 48 | 89 |

From the above result, it is understood that V-70 can give the object adduct in high yield even at 10° C. or 0° C. by prolonging the reaction time.

Examples 6 to 9

The same reaction as in Example 1 except the amount of V-70 used and the reaction time as shown in Table 3 was conducted to give the object adduct.

The result together with that in Example 1 is shown in Table 3.

Control Example 5

The same reaction as in Example 1 except no use of V-70 and the reaction time of 48 hours was conducted to give the object adduct. The result is also shown in Table 3.

TABLE 3

| Example No. | Amount of V-70 (mol %) | Reaction time (hr) | Yield (%) |
| --- | --- | --- | --- |
| Example 6 | 10.0 | 6 | 71 |
| Example 1 | 5.0 | 12 | 79 |
| Example 7 | 1.0 | 48 | 80 |
| Example 8 | 0.5 | 48 | 76 |
| Example 9 | 0.1 | 72 | 67 |
| Control Example 5 | 0 | 48 | not reacted |

From the above result, it is understood that V-70 can act effectively even in 0.1 mol % concentration to give the adduct in high yield.

Example 10

Bromomalononitrile in an amount of 10 mmol, 2-methyl-2-butene in an amount of 10 mmol and methylene chloride in an amount of 10 ml were admixed with one another and V-70 in an amount of 5 mol % was added thereto, followed by conducting a reaction at room temperature (25° C.) for 12 hours with stirring.

After the reaction, the solvent was removed by distillation and the residue was purified by silica gel column chromatography [Packing: Wako Gel C-200 (manufactured and sold by Wako Pure Chemical Industries, Ltd. Trade Name), Eluent: n-hexane/ethyl acetate] to give the object adduct (yield: 81%).

The result is shown in Table 4.

Examples 11 to 19

The same reaction as in Example 10 except using the reactant as shown in Table 4 in place of 2-methyl-2-butene and the reaction time as shown in Table 4 was conducted. The result is also shown in Table 4.

The reaction equation in Examples 10 to 18 is shown below.

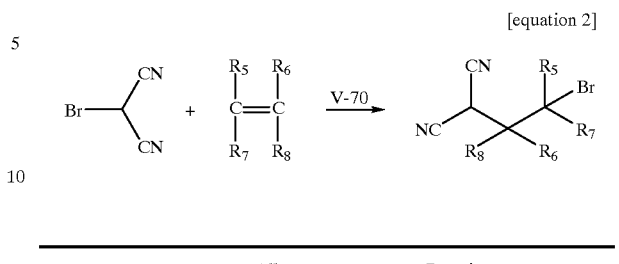

[equation 2]

| | Alkene | | | | Reaction | |
| --- | --- | --- | --- | --- | --- | --- |
| Example No. | $R_5$ | $R_6$ | $R_7$ | $R_8$ | time (hr) | Yield (%) |
| Example 10 | $CH_3$ | $CH_3$ | $CH_3$ | H | 12 | 81 |
| Example 11 | $C_6H_5$ | H | H | $CH_3$ | 72 | 68 |
| Example 12 | $CH_3$ | $CH_3$ | $CH_3$ | $CH_3$ | 12 | 84 |
| Example 13 | $I(CH_2)_8$ | H | H | H | 24 | 78 |
| Example 14 | OAc | H | H | H | 24 | 76 |
| Example 15 | OEt | H | H | H | 24 | 72 |
| Example 16 | Cyclopentene | | | | 24 | 88 |
| Example 17 | Cyclohexene | | | | 24 | 90 |
| Example 18 | Norbornene | | | | 24 | 89 |
| Example 19 | $C_6H_5$ | H | H | H | 12 | 79 |

From the above result, it is understood that the addition reaction of bromomalononitrile to the alkene can give the corresponding object adduct in high yield under such mild condition as room temperature.

While it is reported that bromomalononitrile is not reacted with an alkene containing oxygen-substituted group (i.e. a functional group binding through an oxygen atom such as an alkoxy group and an alkyloxycarbonyl group) such as ethyl-1-propenyl ether upon using AIBN under heating (J.Am.Chem.Soc., 114, 4436 (1992)), it can be understood that the reaction with an alkene containing oxygen-substituted group such as enol derivative (Examples 14 and 15) can also proceed almost quantitatively upon using V-70.

From this fact, the method of the present invention can be understood as superior

Example 20

Bromomalononitrile in an amount of 0.62 g, 1-methoxy-5-methoxycarbonylphenyl-1-pentene in an amount of 1 g and methylene chloride in an amount of 15 ml were admixed with one another and V-70 in an amount of 25 mol % was added thereto, followed by conducting a reaction at room temperature (25° C.) for 2 hours with stirring. After the reaction, the solvent was removed by distillation and methanol was added to the residue, followed by conducting a reaction at the same temperature for 15 minutes with stirring. After the reaction, an aqueous saturated sodium bicarbonate solution in an amount of 10 ml was added to the resultant followed by extracting with methylene chloride, and the solvent was removed by distillation, whereby 1.6 g of crude product was obtained. The crude product was purified to give 1.3 g of the object product.

The result is shown in Table 5.

Control Example 6

Bromomalononitrile in an amount of 10 mmol, 1-methoxy-5-methoxycarbonylphenyl-1-pentene in an amount of 10 mmol and methylene chloride in an amount of 10 ml were admixed with one another and AIBN in an amount of 10 mol % was added thereto, followed by conducting a reaction at room temperature (25° C.) for 24 hours with stirring. After the reaction, the solvent was removed by distillation and methanol was added to the residue, followed by conducting a reaction at the same temperature for 15 minutes with stirring. After the reaction, an aqueous saturated sodium bicarbonate solution in an amount of 10 ml was added to the resultant followed by extracting with methylene chloride, and the solvent was removed by distillation, whereby 1.7 g of crude product was obtained.

The result is also shown in Table 5.

The reaction equations in Example 20 and Control Example 6 are shown below.

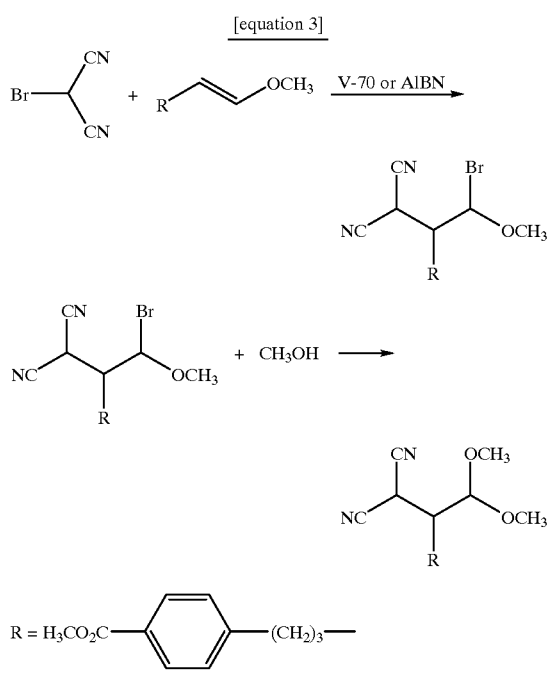

TABLE 5

| Example No. | Radical initiator | Reaction time (hr) | Reaction temperature (° C.) | Yield (%)[1] |
|---|---|---|---|---|
| Example 20 | V-70 | 2 | 25 | 80 (55:45)[2] |
| Control Example 6 | AIBN | 24 | 25 | 55 (10:90)[2] |

[1] yield after column chromatography
[2] a ratio[3] of the object product to by-products
[3] the object product is as follows.

1) yield after column chromatography 2) a ratio[3] of the object product to by-products 3) the object product is as follows.

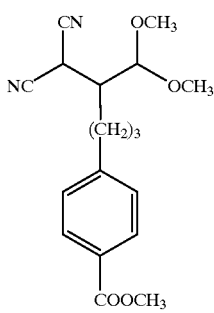

From the above result, it can be understood that the object product can be obtained in higher yield by conducting an addition reaction of bromomalononitrile to 1-methoxy-5-methyloxycarbonylphenyl-1-pentene using V-70 as compared to that of conducting the said reaction using AIBN.

Also from this fact, the method of the present invention can clearly be understood as superior compared with that of the conventional method using AIBN.

Example 21

Styrene in an amount of 10 mmol, methyl bromomalononitrile in an amount of 10 mmol and methylene chloride in an amount of 10 ml were admixed with one another and V-70 in an amount of 10 mol % was added thereto, followed by conducting a reaction at 25° C. for 24 hours with stirring. After the reaction, the solvent was removed by distillation and 2-propanol in an amount of 10 ml was added to the residue to precipitate the object product. The product was recovered by filtration, washed and dried to give the object adduct.

The result is shown in Table 6.

Control Example 7

Styrene in an amount of 10 mmol, methyl bromomalononitrile in an amount of 10 mmol and methylene chloride in an amount of 10 ml were admixed with one another and AIBN in an amount of 10 mol % was added thereto, followed by conducting a reaction at 80° C. for 1 hour with stirring. After the reaction, the solvent was removed by distillation and 2-propanol in an amount of 10 ml was added to the residue to precipitate the object product. The product was recovered by filtration, washed and dried to give the object adduct.

The result is also shown in Table 6.

The reaction equation in Example 20 and Control Example 7 is shown below.

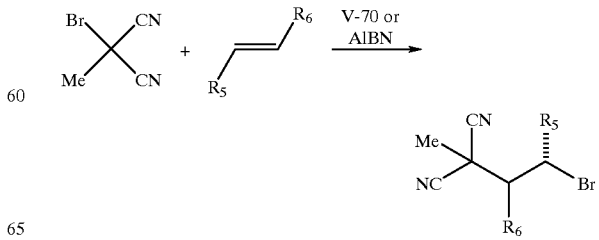

TABLE 6

| Example No. | Radical initiator | Yield (%) | Alkene R$_5$ | R$_6$ | syn | anti |
|---|---|---|---|---|---|---|
| Example 21 | V-70 | 95 | C$_6$H$_5$ | CH$_3$ | 86 | 14 |
| Control Example 7 | AIBN | 95 | C$_6$H$_5$ | CH$_3$ | 50 | 50 |

As is clearly understood from the above result, the addition reaction of methyl bromomalononitrile to styrene using AIBN under heating gives the product having a diastereomeric ratio of 50:50, while the object adduct (syn isomer) can be obtained in a ratio of 86:14 by conducting the reaction using V-70 at room temperature. Namely, it can be understood that the object adduct (syn isomer) can selectively be obtained by using V-70.

As mentioned above, the present invention shows such characteristic effects that it can provide a novel catalyst for the formation of a carbon—carbon bond, a method for the formation of a carbon—carbon bond using the said catalyst and a position-selective addition reaction using the said catalyst and the use of the said catalyst makes it possible to conduct a position-selective addition reaction to an unsaturated bond, which has been difficult, and further the object adduct can be obtained in high yield. Thus, the present invention can give great contribution to this kind of technical field.

What is claimed is:

1. A method for the formation of a carbon—carbon bond comprising reacting an α-halogeno carboxylic acid derivative with an alkene, in the presence of a catalyst shown by the general formula (1):

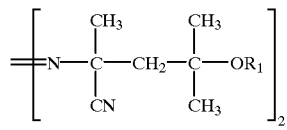
(1)

wherein R$_1$ is a lower alkyl group.

2. A method for an addition reaction with the formation of an additional carbon—carbon bond comprising reacting an α-halogeno carboxylic acid derivative with an alkene in the presence of a catalyst shown by the general formula (1):

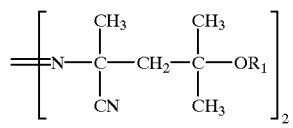
(1)

wherein R$_1$ is a lower alkyl group.

3. A method for production of a compound shown by the general formula (4):

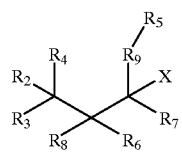
(4)

wherein X is a halogen atom, one of R$_3$ and R$_4$ or both of R$_3$ and R$_4$ are an alkyloxycarbonyl group, an aralkyloxycarbonyl group, an aryloxycarbonyl group, an acyloxy group, an acyl group, a cyano group, a carbamoyl group or a carboxyl group;

R$_2$ is a hydrogen atom, an alkyl group, an aryl group which may have a substituent, an alkoxy group, an aralkyloxy group, an aryloxy group or a hydroxy group, and when one of R$_3$ and R$_4$ is defined as above, the other of R$_3$ and R$_4$ is defined the same as R$_2$;

R$_5$ is a hydrogen atom, an alkyl group, a haloalkyl group, an aryl group which may have a substituent, an aralkyl group which may have a substituent, an aliphatic heterocyclic group, an aromatic heterocyclic group, an alkyloxycarbonyl group, a hydroxyalkyloxycarbonyl group, an aralkyloxycarbonyl group, an aryloxycarbonyl group, an acyloxy group, an acyl group, an alkoxy group, an aralkyloxy group, an aryloxy group, a cyano group, an amino group, a carbamoyl group, a hydroxyl group, a sulfonic acid group, an aldehydo group or a carboxyl group;

R$_6$ is a hydrogen atom, a halogen atom, an alkyl group, an aralkyl group which may have a substituent, an alkyloxycarbonyl group, a hydroxyalkyloxycarbonyl group, a hydroxyl group or a carboxyl group;

R$_9$ is an alkylene group or a bond;

R$_7$ is a hydrogen atom, an alkyl group, a carboxyl group, an alkyloxycarbonyl group, a hydroxyalkyloxycarbonyl group or a hydroxyl group;

R$_8$ is a hydrogen atom, a halogen atom or an alkyl group, and

R$_7$ and R$_8$ may form together an aliphatic ring comprising reacting an α-halogeno carboxylic acid derivative shown by the general formula (2):

(2)

, wherein the symbols have the same meaning as above, with an alkene shown by the general formula (3):

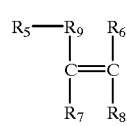
(3)

, wherein the symbols have the same meaning as above, in the presence of a catalyst shown by the general formula (1):

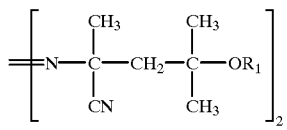

(1)

, wherein $R_1$ is a lower alkyl group,.

4. The method according to claim 1, in which $R_1$ has 1 to 4 carbon atoms.

5. The method according to claim 2, in which $R_1$ has 1 to 4 carbon atoms.

6. The method according to claim 3, in which the halogen atom represented by X in the general formulas (2) and (4) is one selected from chlorine, bromine and iodine;

the alkyloxycarbonyl group represented by $R_3$ and $R_4$ may be straight chain or branched chain and has 2 to 19 carbon atoms;

the aralkyloxycarbonyl group represented by $R_3$ and $R_4$ has 8 to 20 carbon atoms and is derived from carboxylic acids;

the aryloxycarbonyl group represented by $R_3$ and $R_4$ has 7 to 20 carbon atoms;

the acyloxy group represented by $R_3$ and $R_4$ has 2 to 18 carbon atoms;

the acyl group represented by $R_3$ and $R_4$ has 1 to 18 carbon atoms, which is derived from carboxylic acids;

the alkyl group represented by $R_2$ to $R_4$ may be straight chain, branched chain or cyclic and has 1 to 20 carbon atoms;

the alkoxy group represented by $R_2$ to $R_4$ may be straight chain or branched chain and has 1 to 18 carbon atoms;

the aralkyloxy group represented by $R_2$ to $R_4$ has 7 to 20 carbon atoms;

the aryloxy group represented by $R_2$ to $R_4$ has 6 to 20 carbon atoms;

the aralkyl group which may have a substituent represented by $R_5$ and $R_6$ in the general formula (3) has 7 to 20 carbon atoms;

the alkyloxycarbonyl group represented by $R_5$, $R_6$ and $R_7$ may be straight chain or branched chain and has 2 to 19 carbon atoms;

the hydroxyalkyloxycarbonyl group represented by $R_5$, $R_6$ and $R_7$ includes one having 2 to 19 carbon atoms;

the alkyl group represented by $R_5$ may be straight chain, branched chain or cyclic and has 1 to 20 carbon atoms;

the haloalkyl group represented by $R_5$ has 1 to 20 carbon atoms in which the above-mentioned alkyl group is halogenated;

the aliphatic heterocyclic group represented by $R_5$ is a 5- or 6-membered one and has 1 to 3 hetero atoms;

the aromatic heterocyclic group represented by $R_5$ is a 5- or 6-membered one and includes one having 1 to 3 hetero atoms;

the aralkyloxycarbonyl group represented by $R_5$ has 8 to 15 carbon atoms;

the aryloxycarbonyl group represented by $R_5$ has 7 to 20 carbon atoms;

the acyloxy group represented by $R_5$ has 2 to 18 carbon atoms, which is derived from carboxylic acids;

the acyl group represented by $R_5$ has 1 to 18 carbon atoms, which is derived from carboxylic acids;

the alkoxy group represented by $R_5$ may be straight chain or branched chain and has 1 to 18 carbon atoms;

the aralkyloxy group represented by $R_5$ has 7 to 20 carbon atoms;

the aryloxy group represented by $R_5$ has 7 to 15 carbon atoms;

the alkyl group represented by $R_6$, $R_7$ and $R_8$ may be straight chain or branched chain and is a lower alkyl group having 1 to 6 carbon atoms;

the halogen atom represented by $R_6$ and $R_8$ is one selected from chlorine, bromine, fluorine and iodine;

the aliphatic ring formed together by $R_7$ and $R_8$ includes a ring formed through an alkylene group having 3 to 10 carbon atoms, the ring may be monocyclic or polycyclic;

the alkylene represented by $R_9$ may be straight chain or branched chain and has 1 to 10 carbon atoms;

the alkene of the formula (3) may be symmetric or asymmetric and has at least one selected from ethylenically unsaturated aliphatic hydrocarbons having 2 to 20 carbon atoms, unsaturated alicyclic hydrocarbons having 3 to 20 carbon atoms, α-ethelenically unsaturated aromatic hydrocarbons having 8 to 20 carbon atoms, alkenyl esters having 3 to 20 carbon atoms, halogeno-containing ethylenically unsaturated compounds having 2 to 20 carbon atoms, ethylenically unsaturated carboxylic acids having 3 to 20 carbon atoms, ethylenically unsaturated carboxylic acid esters having 4 to 20 carbon atoms, cyano-containing ethylenically unsaturated compounds having 3 to 20 carbon atoms, ethylenically unsaturated amide compounds having 3 to 20 carbon atoms, ethylenically unsaturated aldehydes having 3 to 20 carbon atoms, ethylenically unsaturated sulfonic acids having 2 to 20 carbon atoms, ethylenically unsaturated aliphatic amines having 2 to 20 carbon atoms, ethylenically unsaturated aromatic amines having 8 to 20 carbon atoms, ethylenically unsaturated aliphatic heterocyclic amines having 5 to 20 carbon atoms, ethylenically unsaturated aromatic heterocyclic amines having 5 to 20 carbon atoms, ethylenically unsaturated alcohols having 3 to 20 carbon atoms, ethylenically unsaturated phenols having 8 to 20 carbon atoms; and the lower alkyl group of formula (3) is an alkyl having 1 to 6 carbon atoms.

7. The method according to claim 6, wherein the alkoxy group represented by $R_2$ to $R_4$ may be straight chain or branched chain and has 1 to 8 carbon atoms, and the alkoxy group represented by $R_5$ may be straight chain or branched chain and has preferably 1 to 8 carbon atoms.

8. The method according to claim 1, wherein an amount of the catalyst is in a range generally of 0.01 equivalent or more, relative to the α-halogeno carboxylic acid derivative.

9. The method according to claim 1, wherein an amount of the catalyst is in a range generally of 0.1 to 5 equivalent, relative to the α-halogeno carboxylic acid derivative.

10. The method according to claim 3, wherein the reaction solvent is one selected from the group consisting of hydrocarbons, halogenated hydrocarbons, esters, ketones, and ethers.

11. The method according to claim 3, wherein the reaction temperature is in a range lower than 70° C.

12. The method according to claim 3, wherein the reaction temperature is in a range of −30 to 60° C.

13. The method according to claim 3, wherein the reaction temperature is in a range of −10 to −30° C.

14. The method according to claim 3, wherein the reaction time is suitably in a range of 10 minutes to 170 hours.

15. The method according to claim 3, wherein the position selective addition reaction of the α-halogeno carboxylic acid derivative to the alkene yields predominantly a specific stereo isomer of the compound shown by the above general formula (4).

16. A method for production of a compound shown by the general formula (4'):

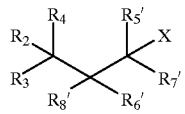

(4')

wherein X is a halogen atom;
one of $R_3$ and $R_4$ or both of $R_3$ and $R_4$ are an alkyloxycarbonyl group, an aralkyloxycarbonyl group, an aryloxycarbonyl group, an acyloxy group, an acyl group, a cyano group, a carbamoyl group or a carboxyl group;
$R_2$ is a hydrogen atom, an alkyl group, an aryl group which may have a substituent, an alkoxy group, an aralkyloxy group, an aryloxy group or a hydroxy group, and when one of $R_3$ and $R_4$ is defined as above, the other of $R_3$ and $R_4$ is defined as the same;
$R_5'$, $R_6'$, $R_7'$ and $R_8'$ are independently a hydrogen atom, a lower alkyl group, a carboxyl group, an aryl group which may have a substituent, a lower alkyloxycarbonyl group, a lower hydroxyalkyloxycarbonyl group or a lower acyloxy group and
$R_7'$ and $R_8'$ may form together an aliphatic ring comprising reacting an α-halogeno carboxylic acid derivative shown by the general formula (2):

(2)

wherein the symbols have the same meaning as above with an alkene shown by the general formula (3'):

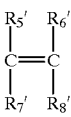

(3')

wherein the symbols have the same meaning as above in the presence of a catalyst shown by the general formula (1):

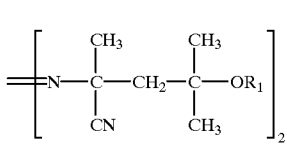

(1)

wherein $R_1$ is a lower alkyl group.

17. The method according to claim 16, in which $R_1$ has 1 to 4 carbon atoms.

* * * * *